United States Patent
Reyes Ramirez et al.

(10) Patent No.: US 12,008,317 B2
(45) Date of Patent: Jun. 11, 2024

(54) SUMMARIZING INFORMATION FROM DIFFERENT SOURCES BASED ON PERSONAL LEARNING STYLES

(71) Applicant: INTERNATIONAL BUSINESS MACHINES CORPORATION, Armonk, NY (US)

(72) Inventors: Perla Guadalupe Reyes Ramirez, Jalisco (MX); Paul Llamas Virgen, Jalisco (MX); Silvia Cristina Santa Ana Velasco, Jalisco (MX); Carolina Garcia Delgado, Jalisco (MX)

(73) Assignee: International Business Machines Corporation, Armonk, NY (US)

( * ) Notice: Subject to any disclaimer, the term of this patent is extended or adjusted under 35 U.S.C. 154(b) by 94 days.

(21) Appl. No.: 16/254,935

(22) Filed: Jan. 23, 2019

(65) Prior Publication Data
US 2020/0233925 A1 Jul. 23, 2020

(51) Int. Cl.
*G06F 40/216* (2020.01)
*A61B 5/16* (2006.01)
*G06F 40/289* (2020.01)
*G06V 10/776* (2022.01)
*G09B 19/00* (2006.01)

(52) U.S. Cl.
CPC ............ *G06F 40/216* (2020.01); *A61B 5/167* (2013.01); *G06F 40/289* (2020.01); *G06V 10/776* (2022.01); *G09B 19/00* (2013.01)

(58) Field of Classification Search
CPC .................................................. G06F 40/289
See application file for complete search history.

(56) References Cited

U.S. PATENT DOCUMENTS

| | | | |
|---|---|---|---|
| 6,499,021 B1 | 12/2002 | Abu-Hakima | |
| 7,877,807 B2 | 1/2011 | Shipp | |
| 8,423,623 B2 | 4/2013 | Li et al. | |
| 8,510,664 B2 | 8/2013 | Rueben et al. | |
| 9,560,152 B1 | 1/2017 | Jamdar et al. | |
| 11,727,935 B2 * | 8/2023 | Malladi et al. | G10L 15/36 |
| 2002/0099775 A1 * | 7/2002 | Gupta et al. | G06F 15/16 |
| 2003/0115550 A1 * | 6/2003 | Womble et al. | G06F 15/00 |

(Continued)

OTHER PUBLICATIONS

Anonymous, "Method and System for Managing Email Threads Based On User Preferences," An IP.com Prior Art Database Technical Disclosure, Jul. 22, 2011, p. 1, IP.com No. IPCOM000208896D.

(Continued)

*Primary Examiner* — James J Debrow
(74) *Attorney, Agent, or Firm* — L. Jeffrey Kelly

(57) ABSTRACT

A method, computer system, and a computer program product for summarizing a piece of information based on a personal learning style of a user is provided. The present invention may include summarizing to the piece of information associated with at least one information source, wherein an output is generated from the summarized piece of information. The present invention may then include generating a summary of the piece of information based on the personal learning style of the user and a plurality of data associated with the user, wherein the personal learning style of the user is determined by a personality test. The present invention may further include presenting the generated summary to the user.

20 Claims, 6 Drawing Sheets

(56) References Cited

U.S. PATENT DOCUMENTS

| | | | |
|---|---|---|---|
| 2004/0249801 A1* | 4/2004 | Kapur | G06F 17/30 |
| 2004/0225667 A1* | 11/2004 | Hu et al. | G06F 17/00 |
| 2005/0262214 A1 | 11/2005 | Bagga et al. | |
| 2007/0226204 A1 | 9/2007 | Feldman | |
| 2007/0245379 A1* | 10/2007 | Agnihortri | H04N 5/445 |
| 2007/0282912 A1* | 12/2007 | Reiner | G06F 17/00 |
| 2009/0006558 A1 | 1/2009 | Taieb et al. | |
| 2012/0136939 A1* | 5/2012 | Stren et al. | G06F 15/16 |
| 2013/0080437 A1* | 3/2013 | Rassi | G06F 17/30 |
| 2013/0339848 A1* | 12/2013 | Mebed | G06F 17/00 |
| 2013/0339849 A1 | 12/2013 | Mebed | |
| 2015/0193400 A1* | 7/2015 | Puvanachandran et al. | G06F 17/22 |
| 2016/0199977 A1 | 7/2016 | Breazeal | |
| 2016/0241499 A1 | 8/2016 | Hailpern et al. | |
| 2018/0077286 A1* | 3/2018 | Raanani et al. | H04M 3/5175 |
| 2018/0239507 A1* | 8/2018 | Bui et al. | G06F 3/0484 |
| 2020/0137224 A1* | 4/2020 | Rakshit et al. | H04M 3/42 |
| 2021/0248326 A1* | 8/2021 | Han et al. | C06F 40/40 |

OTHER PUBLICATIONS

Jain et al., "Method and System for Consuming and Navigating Long Email Threads," An IP.com Prior Art Database Technical Disclosure, Jan. 14, 2015, p. 1-2, IP.com No. IPCOM000240225D, Yahoo!.

Johnson et al., "Generating and Evaluating Summaries for Partial Email Threads: Conversational Bayesian Surprise and Silver Standards," Proceedings of the SIGDIAL 2017 Conference, Aug. 15-17, 2017, p. 263-272, Association for Computational Linguistics, Saarbrucken, Germany.

Mell et al., "The NIST Definition of Cloud Computing," National Institute of Standards and Technology, Sep. 2011, p. 1-3, Special Publication 800-145.

Newman, "Treetables and Other Visualizations for Email Threads," Xerox PARC Technical Report, Sep. 2001, 8 Pages.

Rambow et al., "Summarizing Email Threads," Proceedings of HLT-NAACL 2004, May 2004, 4 Pages.

Ulrich, "Supervised Machine Learning for Email Thread Summarization," The University Of British Columbia Thesis, Sep. 2008, p. 1-69.

Wan et al., "Generating Overview Summaries of Ongoing Email Thread Discussions," Proceedings of the 20th International Conference on Computational Linguistics (COLING '04), Aug. 2004, 7 Pages.

Whittaker et al., "Email Overload: Exploring Personal Information Management of Email," CHI 96 Papers, Apr. 13-18, 1996, p. 276-283, ACM, Vancouver, BC, Canada.

* cited by examiner

SUMMARIZING INFORMATION FROM DIFFERENT SOURCES BASED ON PERSONAL LEARNING STYLES

BACKGROUND

The present invention relates generally to the field of computing, and more particularly to computational linguistics.

When a person is added to a thread of any information or conversation source, such as an email, web page forum or messaging boards, instant messaging, and other forms of digital communication medium, the person may not know about the discussed topic. As such, the person has to read the entire chain of information to better understand the discussed topic. Such a process is very time consuming and, in some cases, the person has to read information multiple times and/or make annotations to fully understand the information. And even after completing this time consuming process, the person may still not fully understand the information or have a different interpretation of the information or the discussed topic.

SUMMARY

Embodiments of the present invention disclose a method, computer system, and a computer program product for summarizing a piece of information based on a personal learning style of a user. The present invention may include summarizing the piece of information associated with at least one information source, wherein an output is generated from the summarized piece of information. The present invention may then include generating a summary of the piece of information based on a personal learning style of the user and a plurality of data associated with the user, wherein the personal learning style of the user is determined by a personality test. The present invention may further include presenting the generated summary to the user.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
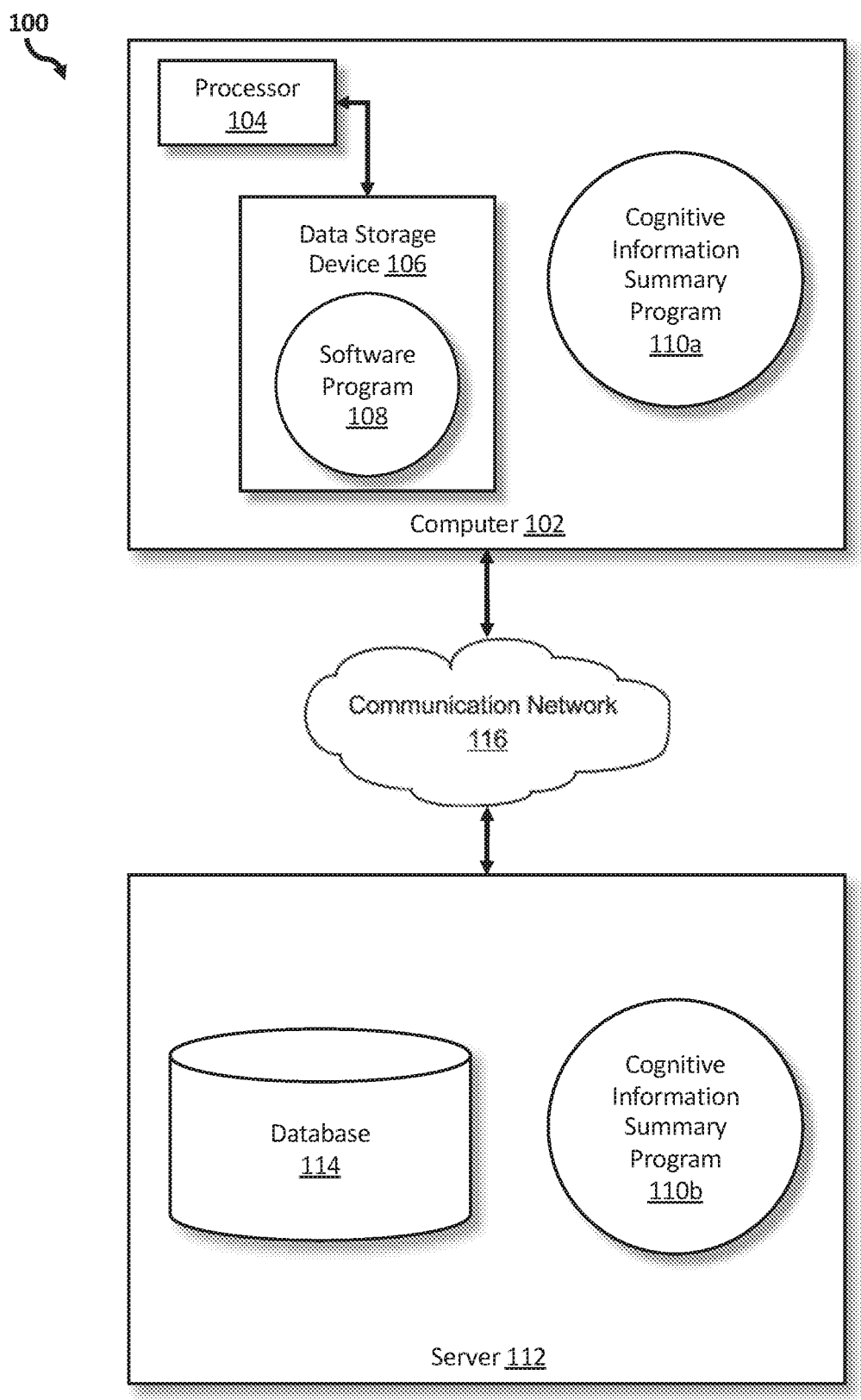
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for summarizing a piece of information based on the personal learning style of a user. As such, the present embodiment has the capacity to improve the technical field of computational linguistics by analyzing and summarizing at least one piece of information from at least one information source, and then generating an information summary based on the personal learning style of the user and the data associated with the user on the user profile. More specifically, the cognitive information summary program may identify the user, and then determine whether a personality test is necessary to determine the personal learning style of the user. The cognitive information summary program may then receive at least one information source from the user, which the cognitive information summary program utilizes at least one application program interface (API) to analyze and summarize. The summarizing of the piece of information includes the most used words by the user and any other important data included in the user profile associated with the identified user. The analyzed and summarized piece of information may then be converted into a form of information summary based on the personal learning style of the user. The cognitive information summary program may then present the information summary to the user. The cognitive information summary program may then request feedback from the user to learn the effectiveness of the summary.

As previously described, when a person is added to a thread of any information or conversation source, such as an email, web page forum or messaging boards, instant messaging, and other forms of digital communication medium, the person may not know about the discussed topic. As such, the person has to read the entire chain of information to better understand the discussed topic. Such a process is very time consuming and, in some cases, the person has to read information multiple times and/or make annotations to fully understand the information. And even after completing this time consuming process, the person may still not fully understand the information or have a different interpretation of the information or the discussed topic.

As such, in many cases, reading the chain of information does not lead to a complete or even better understanding of the discussed topic, since each person possess different learning styles or characteristics to learn and comprehend information. A majority of people are categorized as visual learners (i.e., people who learn better with images, videos or some form of visual stimuli), auditory learners (i.e., people who learn better with audio files and recordings or some form of auditory stimuli), or kinesthetic learners (i.e., people who learn better when focused on emotions or feelings).

Therefore, it may be advantageous to, among other things, summarize the thread of any information and/or conversation, such as an email, web page forum or messaging boards, instant messaging, and other forms of digital communication medium, and provide a summary based on the personal learning style of the user (e.g., Neuro-Linguistic Programming Personality Types (NLP), which may include visual, auditory and kinesthetic types as NLP types). As such, based on a user's personal learning type (e.g., NLP type), the output of information may be in a form (e.g., auditory records, images, videos) that the user may be able to better comprehend in order to extrapolate the necessary information from the thread. Therefore, it may be easier for the user to understand a topic and may reduce the time of reading and/or responding to a thread of information.

According to at least one embodiment, the cognitive information summary program may send a brief personality test to a user. The cognitive information summary program may utilize different learning style assessment tests (i.e., personality tests). The answers to the brief personality test provided by the user may then be utilized to determine the personal learning type (e.g., NLP type) of the user.

According to at least one embodiment, the cognitive information summary program may receive, as inputs, by the user, results from a recent personality test, at least one thread of information, and words most used by a person in the thread of information and/or the user. The cognitive information summary program may then summarize the at least one thread of information and provide, as an output, an information summary (i.e., a summary) based on the type of person, or personal learning style (e.g., NLP type) of the user (i.e., based on the results of the personality test).

According to at least one embodiment, the cognitive information summary program may identify the most used words (e.g., phrases, terms, individual nouns or verbs) by the person throughout the thread of information. The cognitive information summary program may then utilize the most used words in the summary. The present embodiment may include utilizing the most used words (e.g., phrases, terms, individual nouns or verbs) by the user based on previous threads of information.

In the present embodiment, the user may have the option of changing the type of personal learning style, or the way of presenting the summary at any time. For example, if the user is receiving auditory recordings to summarize information and the user decides that images would be more helpful for a particular thread of information, then the user may change the summary to generate images or visual summaries of the thread of information rather than auditory recordings.

According to at least one embodiment, the user may give feedback (e.g., provide a score) for the cognitive information summary program after the user receives the summary. The feedback (i.e., user feedback) may be based on whether the user possesses a better understanding of the discussed topic after receiving and utilizing the summary generated by the cognitive information summary program. Based on the user feedback and the historical data of the previous summary, the cognitive information summary program may improve summaries provided to the user in the future.

According to at least one embodiment, the cognitive information summary program may be utilized to summarize information from a book, magazine or any information source in a digital file format. Rather than reading a book, for example, the cognitive information summary program may convert the digital file into a summary based on the personal learning style of the user. The cognitive information summary program may first convert the file into the best form of summary based on the personal learning style of the user. For analysis, the input (i.e., digital file) may be in an understandable or base language or text. For example, when the input is audio, then the cognitive information summary program may utilize a speech-to-text engine (e.g., IBM Watson® Speech to Text (IBM Watson and all IBM Watson-based trademarks and logos are trademarks or registered trademarks of International Business Machines Corporation and/or its affiliates)) to convert the information into text. In addition, the cognitive information summary program may combine the output from the speech-to-text engine with an image recognition engine (e.g., IBM Watson® Visual Recognition (IBM Watson and all IBM Watson-based trademarks and logos are trademarks or registered trademarks of International Business Machines Corporation and/or its affiliates)) to convert the information into images or visual representations.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a cognitive information summary program 110a. The networked computer environment 100 may also include a server 112 that is enabled to run a cognitive information summary program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 4, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the cognitive information summary program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the cognitive information summary program 110a, 110b (respectively) to generate a cognitive information summary based on the personal learning style of a user. The cognitive information summary method is explained in more detail below with respect to FIGS. 2 and 3.

Figure 2:
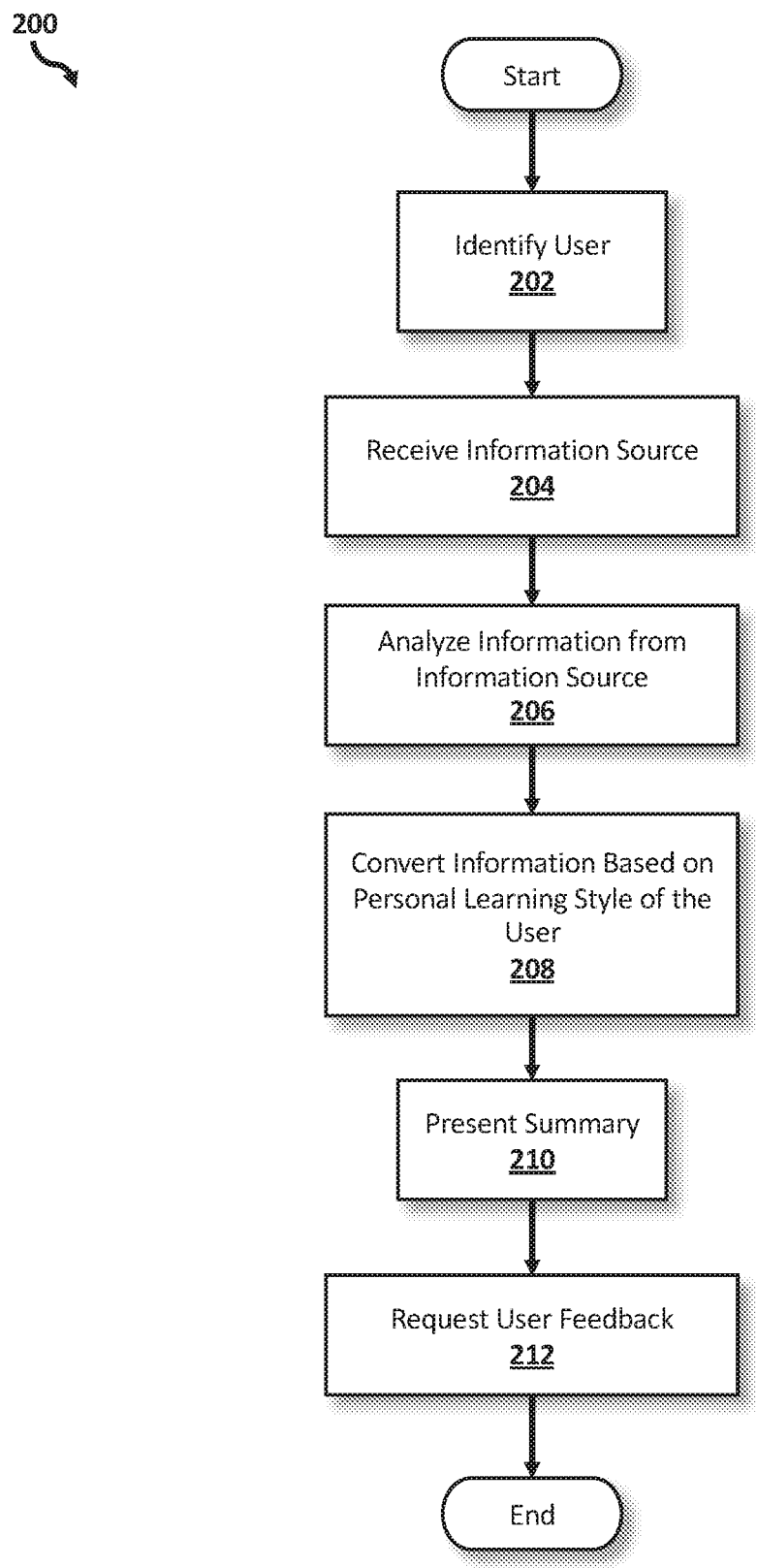
FIG. 2 is an operational flowchart illustrating a process for cognitive information summarization according to at least one embodiment.

Referring now to FIG. 2, an operational flowchart illustrating the exemplary cognitive information summary process 200 used by the cognitive information summary program 110a, 110b according to at least one embodiment is depicted.

At 202, a user is identified. The cognitive information summary program 110a, 110b may identify the user by prompting the user (e.g., via dialog box) to provide the user name and password associated with the user. The dialog box, for example, may include a label "Username" with a blank comment box to the right, and a label "Password" with a blank comment box to the right. Once the user enters the user name and password associated with the user, the user may select the "Submit" button located at the bottom of the dialog box. Each user name and password may be associated with a user profile (i.e., personal profile), which is stored on a profile database (e.g., database 114) associated with the cognitive information summary program 110a, 110b.

If, however, the user is first-time user, then, according to at least one implementation, the user, for example, may click the "First-Time User" button located to the left of the "Submit" button in the dialog box. The user may then be prompted (e.g., via dialog box) to create a user profile with personal characteristics of the user (e.g., full name, preferred name, email address, age, gender, preferences). Once the user finishes setting up the user profile, then the user may click the "Finish" button located on the bottom of the dialog box. The created user profile may then be stored on the profile database.

In the present embodiment, if the user is a first-time user, then the cognitive information summary program 110a, 110b may transmit, via communication network 116, a brief personality test to the user. The cognitive information summary program 110a, 110b may utilize different learning style assessment tests (i.e., personality tests), such as a forced-choice personality test (e.g., Riso-Hudson Enneagram Type indicator (RHETI)), Grasha-Riechmann Student Learning Style Scales, Paragon Learning Style, Kolb's Learning Style Inventory (LSI) questionnaires, a Visual Aural Read-Write and Kinesthetic (VARK) learning style questionnaire, Jackson's Learning Styles Profiler (LSP), various online learning style quizzes, and another standard personality test. Based on the answers provided by the user, the cognitive information summary program 110a, 110b may determine the personal learning style of the user. The results of the personality test and the determined personal learning style of the user may be saved under the applicable user name and password, and stored in the profile database. A detailed operational flowchart of the personal learning style determination process 300 in the cognitive information summary program 110a, 110b will be described in greater detail below with respect to FIG. 3.

In the present embodiment, if the user is a return user, then the cognitive information summary program 110a, 110b may retrieve the personal learning style of the user from the user profile. If, however, the cognitive information summary program 110a, 110b, according to at least one implementation, determines that there is an error or discrepancy with the personal learning style of the user and the actions of the user (e.g., user feedback, user skips videos generated by the cognitive information summary program 110a, 110b) that may affect the accuracy of the personal learning style determined by the cognitive information summary program 110a, 110b, then the cognitive information summary program 110a, 110b may commence the personal learning style determination process 300 as described in greater detail below with respect to FIG. 3 by prompting the user to respond to a personality test and re-evaluate the previously determined personal learning style associated with the user. Since the user's personal learning style may be a merger or combination of multiple personal learning styles, re-evaluating the previously determined personal learning style of the user may improve the accuracy of the cognitive information summary program 110a, 110b.

In at least one embodiment, the cognitive information summary program 110a, 110b may periodically prompt the return user to respond to a personality test and re-evaluate or confirm the previously determined personal learning style associated with the user. In another embodiment, the user may request a new personality test at any time, thereby prompting the cognitive information summary program 110a, 110b to proceed with the personal learning style determination process 300 as described in greater detail below with respect to FIG. 3. By clicking the "New Personality Test" button, for example, located on the bottom of the main screen, the user may request a new personality test.

Additionally, each time that the user logs into the cognitive information summary program 110a, 110b with the same user name any generated data (e.g., user historic data, key words, irrelevant words, personality test results, personal learning style, previous user actions) may be saved on the profile database of the cognitive information summary program 110a, 110b. Additionally, the user profile may be created, modified or updated by the user or service providers.

For example, the user is a return user. Therefore, the user enters the user's user name "RUGBYQA1782," associated password, and clicks the "Submit" button. The cognitive information summary program 110a, 110b then retrieves the user profile associated with "RUGBYQA1782." The cognitive information summary program 110a, 110b determines that a new personality test is unnecessary at this time for the user.

In another embodiment, the user may be identified once the cognitive information summary program 110a, 110b is loaded on a user device. Once the user opens the main screen for the cognitive information summary program 110a, 110b, the user may be prompted (e.g., via dialog box) to confirm the identification of the user. The user's user name is presented at the top of the dialog box, with "Yes" or "No" buttons underneath. If the user's user name matches the user name presented in the dialog box, the user may select the "Yes" button and the cognitive information summary program 110a, 110b retrieves the user profile associated with the identified user. If, however, the user name did not match the user's user name, then the user may click the "No" button in which another dialog box may appear for the user to include the user's user name for the cognitive information summary program 110a, 110b to retrieve the correct user profile associated with the user.

In the present embodiment, the cognitive information summary program 110a, 110b may include any new personality test results in the user profile stored on the profile database. In at least one embodiment, the new personality test results are merely listed in the user profile and only the newest personality test results may be utilized to determine the personal learning style of the user. In another embodiment, the new personality test results are calculated into, or factored into the previous personality test results to determine the personal learning style associated with the user.

Next, at 204, at least one information source is received. Using a software program 108 on the user device (e.g., user's computer 102), the cognitive information summary program 110a, 110b may receive, as an input, at least one information source via communication network 116. The received at least one information source may include articles, publications, magazines, books, emails (e.g., a thread of multiple emails), daily user's tasks, instant messaging, short message service (SMS), social media posts (e.g., a thread of multiple comments related to one or a series of social media posts) multimedia message service (MMS), web page forums or messaging boards, videos and other forms of communication in digital file format. The digital file format associated with the received at least one information source may be uploaded from an information database (e.g., database 114), from a website, or the user device. Alternatively, the user may manually enter the at least one information source into the cognitive information summary program 110a, 110b.

Continuing the previous example, RUGBYQA1782 transmits a series of email related to a current employment assignment, approximately 15 pages long, into the cognitive information summary program 110a, 110b. The series of emails include an ongoing conversation between 10 different employees in four different departments related to the details of the work assignment. The earliest email was received three days ago and the newest email was 30 minutes prior to RUGBYQA1782 noticing the series of emails. Today is RUGBYQA1782's first day returning to work after a two-week vacation, where RUGBYQA1782 had very limited email access.

Then, at 206, information from the information source is analyzed. Utilizing an application program interface (API), the cognitive information summary program 110a, 110b may analyze and summarize the received information source. The API may identify the topic discussed in the information source, extract relevant information from the information source, discard any irrelevant information, and identify any repetitive sentences, terms, phrases or key words. The cognitive information summary program 110a, 110b may utilize several different types of APIs, such as an API that transcribes audio files into written text files (e.g., IBM Watson® Speech to Text), an API that transforms written text files into audio files (e.g., IBM Watson® Text to Speech (IBM Watson and all IBM Watson-based trademarks and logos are trademarks or registered trademarks of International Business Machines Corporation and/or its affiliates)), an API that tags, classifies and searches visual content using machine learning (e.g., IBM Watson® Visual Recognition), an API that predicts personality characteristics, needs and values through written text (e.g., IBM Watson® Personality Insights (IBM Watson and all IBM Watson-based trademarks and logos are trademarks or registered trademarks of International Business Machines Corporation and/or its affiliates)), and an API that detects emotional and language tones in written text (e.g., IBM Watson® Tone Analyzer (IBM Watson and all IBM Watson-based trademarks and logos are trademarks or registered trademarks of International Business Machines Corporation and/or its affiliates)).

Additionally, the API may search, or provide the cognitive information summary program 110a, 110b with a software program 108 to search, the information database for information already stored on the identified topic (i.e., topic discussed). The previously stored information on the identified topic may be compared with the recent information received, and suggestions may be provided on additional pieces of information to be included with the recent information received. In at least one embodiment, the API may search, or provide the cognitive information summary program 110a, 110b with a software program 108 to search, the internet for additional pieces of information to add context to the recent information received. In another embodiment, the API may search, or provide the cognitive information summary program 110a, 110b with a software program 108 to search, information in the user profile associated with user for additional pieces of information associated with the recent information received on the identified topic. If the user previously input information related to the recent information received, then the previously input information may be utilized to add context to the recent information received. For example, if the information source includes a thread of instant messages from the user's relatives in regards to who has a recipe for chocolate chip cookies, and the user previously engaged in several of text messages with a cousin who stated that their uncle bakes the best chocolate chip cookies, then the API may use that previous series of text messages to add a comment that their uncle was previously credited with baking the best chocolate chip cookies.

As an output of the APIs (i.e., output of the APIs may be generated by the software program(s) 108 provided by the APIs to perform a specific function or task, or by the APIs directly), the cognitive information summary program 110a, 110b may receive a list of key words, repetitive words or sentences, summary suggestions based on the preferences of the user (i.e., user preferences), and/or insights associated with the identified topic. The user preferences may include the type of personality (e.g., auditory, visual, kinesthetic) that the user may change at the discretion of the user, or may be combined with one or more types of personality based on the results from the recent and/or previous personality test results. In some embodiments, the list of key words may include references to the location (i.e., pointers) of each key word in the received information source.

In some embodiments, the repetitive words or sentences may be sorted based on the preferences of the user (e.g., sorted in a list from highest to lowest frequency, sorted in a list from lowest to highest frequency). In at least one embodiment, the repetitive words or sentences may be presented with a percentage of usage. In the present embodiment, the user may include as a preference to exclude any repetitive words or sentences that are below a certain frequency number (e.g., any repetitive words or sentences with a frequency number below 10% are excluded from the list).

In some embodiments, the summary suggestions provided by the API may be based on the personal learning style of the user as indicated in the user profile associated with the user. For example, if the user prefers information in a visual medium since the user is a visual learner, then the API may include suggestions on images related to the relevant words. In some embodiments, the API may also create an affinity diagram segregating by topic and ordering the images with the appropriate sentences to add context to the images. Then, the information, with the corresponding images, may be presented in a summary chart (i.e., a brief summary of the information which may be utilized by the cognitive information summary program 110a, 110b to generate an information summary based on the personal learning styles of the user). An example of a summary chart is provided below.

In some embodiments, the cognitive information summary program 110a, 110b may determine the words most used by the user based on the historical data associated with the identified user in the user profile, and may use these most used words in the summary of the analyzed information. The cognitive information summary program 110a, 110b may determine the most used words of the user by reviewing a history of multiple information sources (e.g., emails, social messaging boards, instant messaging), as well as any information from the user profile. For example, if the user is an engineer, the cognitive information summary program 110a, 110b may utilize more technical words associated with the specific discipline of engineering that the user is involved in.

In some embodiments, the cognitive information summary program 110a, 110b may also, based on the privacy settings of the user, have access to any company profile associated with the user, social media profiles, any other profiles associated with the user, and information pertaining to the user's employer, profession and/or occupation, one or more email accounts associated with the user, and employer related chats and/or instant messaging services. For the cognitive information summary program 110a, 110b to gain any access to any company profile associated with the user, social media profiles, any other profiles associated with the user, information pertaining to the user's employer, profession and/or occupation, one or more email accounts associated with the user, and employer related chats and/or instant messaging services, the user may have to affirmatively allow the cognitive information summary program 110a, 110b to access such information. If the user fails to respond to a prompt (e.g., via dialog box) requesting such access, or blocks (i.e., denies) such access (i.e., the user may deny all or some access to specific profiles, email accounts, chat and/or instant messaging services, or information associated with the user and/or user's employer), then the cognitive information summary program 110a, 110b may be prohibited to access to such information, email accounts, profiles or chat and/or instant messaging services. Additionally, the user may revoke, modify or allow access at any time, and the cognitive information summary program 110a, 110b may, in real-time, prompt (e.g., via dialog box) the user when the cognitive information summary program 110a, 110b is about to access specific profiles, email accounts, chat and/or instant messaging services, or information associated with the user and/or user's employer, even if the user already granted access to such specific profiles, email accounts, chat and/or instant messaging services, or information associated with the user and/or user's employer. The user may then revoke, modify, or change the user privacy settings associated with the access by, for example, selecting the "Modify" button located in the dialog box. The cognitive information summary program 110a, 110b may then pause or suspend any access to specific profiles, email accounts, chat and/or instant messaging services, or information associated with the user until the user has completed the modification, confirmed that the modification is accurate and effective immediately, and the dialog box has disappeared.

In at least one embodiment, if the information associated with the first user includes information associated with second user and/or employer, the cognitive information summary program 110a, 110b may have to receive affirmative permission from the second user and/or employer to access such information. Failure to receive such affirmative permission from the second user and/or employer may prohibit the cognitive information summary program 110a, 110b from accessing any information related to the second user and/or employer. If, however, the first user affirmatively allows access to such information and the second user declines such access, the cognitive information summary program 110a, 110b may access information only associated with the first user and block access to any information related to the second user. The cognitive information summary program 110a, 110b may then prompt (e.g., via dialog box) the first user as to whether the cognitive information summary program 110a, 110b may proceed with the access of allowed portions of the information, if the second user has declined access. The first user may then confirm that the cognitive information summary program 110a, 110b should proceed with access (although such access only relates to the information associated with the first user) or deny such access altogether.

In some embodiments, the cognitive information summary program 110a, 110b may utilize an extraction engine to extract key words from the text associated with the information from the at least one information source.

In one embodiment, depending on the analyzed information, the summary chart and/or list may be divided into multiple boxes or categories (e.g., understanding the problem or key topic discussed, necessary actions for a solution and root cause and lessons learned, any associated audio recordings, videos, games or images corresponding with any of the boxes or categories). For example, if the thread of emails is related to the inclusion of an improper label for a product, then the summary chart and/or list is as follows:

Subject 1: Understand the Problem

The label printed with the wrong compliance requirements and missing one P label to be read with a scanner in Storage. The brands and products affected are Storage and Power.

Subject 2: Necessary Actions for a Solution

Label was reworked by Employee A to include the appropriate marks on the label according to the compliance requirements.

Subject 3: Root Cause and Lessons Learned

Development picked up the Product Number (PN) without reviewing the compliance requirements and the equipment needed at Storage to use this PN.

For the above summary chart/list, if the user was a visual learner, then the cognitive information summary program 110a, 110b may include a picture of the improper label with a red "X" next to that improper label, and a picture of the proper or corrected label with a green checkmark next to the proper label. In addition, a flowchart with the process followed that lead to the creation of the improper label indicating the root cause of the labelling error, and a new flowchart with the process that will be followed in order to avoid such a labelling error in the future may be depicted.

Continuing the previous example, the cognitive information summary program 110a, 110b utilizes three APIs, the IBM Watson® Tone Analyzer, the IBM Watson® Text to Speech and the IBM Watson® Visual Recognition, to analyze and summarize the series of emails. The IBM Watson® Tone Analyzer is utilized to analyze the different tones used by each of the senders, the IBM Watson® Text to Speech is utilized to analyze the text and translate the text into an audio recording and the IBM Watson® Visual Recognition is utilized to analyze the various photographs of the different products and brands included in the emails. The APIs generate the following output:

Identified Topic:

New Work Assignment to evaluate the success of the top 2 brands of widgets manufactured by employer for an upcoming sales meeting.

List of Key Words:

Brand A, Brand B.

Repetitive Words or Sentences:

Brand A (45%), Brand B (25%), Brand C (5%), Brand D (5%), Brand E (3%).

Brand A recently had a steep decline in sales (31%), Brand C recently had an incline in sales due to Valentine's Day (15%), Brand D was very popular among a younger demographic in the summer months (10%), Brand B has always been a top seller (5%).
Summary Suggestions:

Provide sales history on the brands, including if the sales of each brand is consistent or fluctuates over a calendar year.
Insights:

A recent email (in a separate thread of emails) with the reported sales of each brand of widgets manufactured by the employer during the past calendar year; another email (in a separate thread of emails) with the projected sales of each brand of widgets manufactured by the employer in the upcoming calendar year; recent set of advertisements on social media for a competitor company's widgets that are similar to Brand E that recently has more than 800,000 views and 300,000 likes or shares.

Since RUGBYQA1782 is a part of the accounting and sales department, RUGBYQA1782's preferences include providing historical data associated with the sales of the brands to determine the top two brands of widget.

Then, at 208, the information is converted based on the personal learning style of the user. Utilizing a converter, the analyzed information and generated output (e.g., list of key words, repetitive words or sentences, summary suggestions based on user preferences, insights associated with the identified topic) may be converted into an information summary (i.e., summary) based on the personal learning style of the user. The personal learning style of the user (e.g., neuro-linguistic personality (NLP) type) may be based on the results of the most recent, or combination of a series of, personality tests taken by the user. A detailed operational flowchart of the personal learning style determination process 300 in the cognitive information summary program 110*a*, 110*b* will be described in greater detail below with respect to FIG. 3.

The cognitive information summary program 110*a*, 110*b* may utilize several different types of converters, as such as a high speech converter to transcribe audio files into written text files (e.g., IBM Watson® Speech to Text), a high speech converter to transform written text files into audio files (e.g., IBM Watson® Text to Speech), a converter that tags, classifies and searches visual content using machine learning (e.g., IBM Watson® Visual Recognition), a converting service that predicts personality characteristics, needs and values through written text (e.g., IBM Watson® Personality Insights), and a converting service that detects emotional and language tones in written text (e.g., IBM Watson® Tone Analyzer). In some embodiments, the APIs utilized to analyze the information from the received source of information may also be utilized as the converter.

In the present embodiment, the cognitive information summary program 110*a*, 110*b* may retrieve the personal learning style of the user from the user profile stored in the profile database, which may include, among other data associated with the user, the personal learning style of the user. Once the personal learning style of the user is retrieved, the cognitive information summary program 110*a*, 110*b* may transmit the data associated with the personal learning style of the user to the converter via communication network 116. The converter may then utilize the data transmitted on the personal learning style of the user to the determine the form (e.g., images, videos, games, audio recordings) of the summary to be presented to the user.

In the present embodiment, the converter may utilize the output generated by the APIs (e.g., list of key words, repetitive words or sentences, summary suggestions based on user preferences, insights associated with the identified topic) to determine the context of the information summary. The summary suggestions may provide the general context (i.e., frame or information related to main idea/identified topic) that should be included in the information summary. The summary suggestions may also provide possible images or videos that may be included in the information summary depending on the personal learning style of the user. For example, the summary suggestions will include a proper label and an improper label of the same product, if the identified topic of the information is identifying issues with product labeling. The converter may also utilize the output including the list of key words and repetitive words or sentences to incorporate the same terminology or images into the information summary. Based on the rank (e.g., the percentage of usage) of the repetitive words or sentences, the converter may include higher ranked (e.g., words or sentences with a higher percentage of usage) words or sentences rather than lower ranked (e.g., words or sentences with a lower percentage of usage) words or sentences. If the converter transforms the information into images or a visual summary, then the repetitive words or sentences may be included with the appropriate images to provide context for the images. For example, if the phrase "improper label" is repetitively associated with a particular label, then the converter will identify that particular label as the "improper label." The converter may utilize the insights related to the identified topic to add context to the summary. For example, if several members of the distribution department stated in the information provided that the issue is directly related to improper labeling, then the converter will determine that improper labeling is an important part of the summary and therefore, images or text related to improper labeling should be included in the information summary.

In the present embodiment, the converter may utilize the output generated by the APIs to determine whether any images, diagrams or other form of visual representation is important to the identified topic and may be included in the information summary. If, based on the summary suggestions, list of key words or repetitive sentences, identified topic, or insights related to the identified topic the visual representation is identified as irrelevant, then the visual representation may be considered unimportant and excluded from the information summary. In at least one embodiment, any visual representation (e.g., image, table, chart or diagram) included in the information may be included in the information summary. If the visual representation is considered unimportant or irrelevant based on the output generated by the APIs, then the converter may include a link (for visual and kinesthetic learners) or a separate audio file (for auditory learners) labeled as, for example, "Additional Information," to include such visual representation in visual or audio format depending on the personal learning style of the user.

In at least one embodiment, if the user is a visual learner and no visual representations were provided in the information or no visual representations were identified as relevant in the information, then the converter may retrieve related images from a database or internet to generate the visual summary for the user. For example, if the summary is related to including the wrong product number on a label, then the visual summary will include a first box with the improper product number. On top of the first box, the converter includes a red "X," and a second box with the proper product number. On top of the second box, the converter includes a green check mark. Therefore, the converter transforms the written text on improper labeling with a visual representation identifying the mislabeling issue as including the wrong product number in the label, and utilize the boxes and the red "X" and green check mark to distinguish the wrong product number and the correct product number.

In at least one embodiment, if the user is an auditory learner, then the converter may convert a summary of the written text generated by the output of the APIs into an audio file or recording. For example, the audio file will simply state, "the identified topic is the improper labeling of Product XYZ. At some point, the wrong product number of 123456 was included on the label related to Product XYZ instead of the correct product number 654321." If any visual representations are included in the information that user is able to access (i.e., depending whether the visual representation is included as a separate audio file or excluded from conversion since the visual representation was identified as irrelevant), then the converter may transform the visual representation into an audio recording. The audio recording may describe the visual representation and may identify the source from which the visual representation is derived from. For example, if a visual representation of the improper label was included in the information, then the converter will translate a description of the improper label into an audio recording, stating, "The top right side of the label includes Product Name XYZ and the top left side of the label includes Serial Number 56GH56IKZ . . . "

Continuing the previous example, the cognitive information summary program 110*a*, 110*b* previously determined that RUGBYQA1782 is a kinesthetic learner based on the NLP personality type. As such, RUGBYQA1782 comprehends and understands information when presented in an interactive form of summary, such as a simple interactive game. As such, the cognitive information summary program 110*a*, 110*b* utilize a high speed converter that searches the internet for images of Brand A, Brand B, Brand C, Brand D and Brand E. The converter further transforms the sale history of each of the brands into a line graph in which the sale related to each brand is plotted onto the line graph over the calendar year, and another line graph for the projected sales of each brand in the upcoming calendar year.

Then, at 210, a summary is presented. The summary generated by the cognitive information summary program 110*a*, 110*b* may be presented to the user, in the form determined to be best for the user based on the personal learning style of the user.

In the present embodiment, the user may change the form of the summary presented. For example, if the presented summary includes images, the user may prefer an audio based summary when the user is driving and unable to view images at that time. The user may, via virtual assistant, audio-enabled device, or clicking a "Change Summary" button, for example, located on the bottom of the screen when the summary is presented, change the form of the summary. The user may be prompted, via dialog box or computer generated voice command, to select a new form of summary (e.g., audio, visual or kinesthetic).

Continuing the previous example, the cognitive information summary program 110*a*, 110*b* displays a visual summary in which RUGBYQA1782 connects the discussed brands of widgets with the respective reported and projected sales as shown on the line graphs generated by the converter. When RUGBYQA1782 clicks on the respective reported or projected sales, then additional details on any fluctuations or trends of the sales history of each brand is outlined. When RUGBYQA1782 hovers over the name of the brand, the comments from the different employees associated with each brand are provided. Any brand with additional information pertaining to the popularity of similar widgets from competitors or the brand itself, including recent advertisements or social media posts or comments, will be highlighted in yellow. When RUGBYQA1782 clicks the name of the brand, another page will appear in which RUGBYQA1782 may access the additional videos, images or social media posts related to the brand or similar competing brand. After five minutes of reviewing the visual summary, the cognitive information summary program 110*a*, 110*b* prompts RUGBYQA1782 to start a simple interactive game with questions related to the visual summary presented.

However, since RUGBYQA1782 is getting dressed for work and unable to perform the simple interactive game at this time, RUGBYQA1782 verbally commands RUGBYQA1782's virtual assistant device to change the summary to audio. As such, the cognitive information summary program 110*a*, 110*b* changes the form of the summary into an audio recording. An image of an audio player appears on RUGBYQA1782's smart phone, and the audio recording generated by cognitive information summary program 110*a*, 110*b* plays the summary for RUGBYQA1782.

In another embodiment, the simple interactive game may include a visual summary of the information, and the cognitive information summary program 110*a*, 110*b* may include a series of questions. The user may respond to each question by, for example, clicking a "Yes" or "No" button and reinforce the information provided. For example, if the user selects the incorrect response, then a red "X" next to that incorrect response will be shown, and if the user selects a correct response, then a picture of a green checkmark next to the correct response will be shown. As such, the interactive game generated for a user with a kinesthetic personal learning style may include simple questions to reinforce the user's understanding of the information provided, as well as keep the user engaged in reading and reviewing the information provided. For example, the interactive game is a relation game in which the cognitive information summary program 110*a*, 110*b* generates a column with the brand images (Column A), and another column with the brand descriptions in a different order (Column B), and the user has to relate the brand images in Column A with the correct brand descriptions in Column B. As such, the cognitive information summary program 110*a*, 110*b* may need minimal, if any, programming to provide a simple interactive game for the user.

In another embodiment, the summary created for a kinesthetic learner may be similar to the summary created for a visual learner. The cognitive information summary program 110*a*, 110*b* may present a visual summary of the information, and after a certain period of time, the cognitive information summary program 110*a*, 110*b* may present questions to reinforce the information presented to the user. In at least one embodiment, the cognitive information summary program 110*a*, 110*b* may give the user five minutes to review the visual summary presented, and then prompt (e.g., via dialog box) the user to participate in a simple interactive game (e.g., respond to a series of questions about the information presented). The dialog box, for example, will include "Yes" or "No" buttons for the user to respond to and indicate whether the user wants to participate in the simple interactive game. If the user clicks the "Yes" button, then the dialog box will disappear and the game will proceed. If, however, the user clicks the "No" button, then the dialog box will disappear and the visual summary will reappear. In at least one other embodiment, the default time of five minutes may be re-configured or changed by an administrator or the user.

In another embodiment, a kinesthetic learner may commence the simple interactive game at any time after the visual summary is presented. The user may, for example, click on any part of the visual summary, or click on any key of the mobile device, and the user will be prompted, via dialog box, to participate in the simple interactive game. The dialog box will include "Yes" or "No" buttons for the user to respond to and indicate whether the user wants to participate in the simple interactive game. If the user clicks the "Yes" button, then the dialog box will disappear and the game will proceed. If, however, the user clicks the "No" button, then the dialog box will disappear and the visual summary will reappear.

Then at 212, user feedback is requested. The user feedback may be utilized by the cognitive information summary program 110a, 110b to determine the effectiveness of the displayed summary. The cognitive information summary program 110a, 110b may prompt (e.g., via dialog box) the user to provide user feedback in which the user may provide comments associated with the usefulness of the cognitive information summary program 110a, 110b. In some embodiments, the user may provide a score (i.e., normalized quantity from 1 to 10) on the effectiveness of the cognitive information summary program 110a, 110b, as well as provide comments to further explain the reason for the score given. Based on the user feedback, the cognitive information summary program 110a, 110b may determine whether the form of the summary, context of the summary, or determined personal learning style of the user may be re-evaluated or modified.

In some embodiments, the user may be prompted by at least two forms of notification (e.g., visual via dialog box, audio via loud alert, touch via vibration of the user device) to provide user feedback simultaneously to when the summary is displayed at 210. In other embodiments, the summary may be presented at 210 first and then user may be prompted to provide user feedback shortly thereafter.

In the present embodiment, the user may opt out of providing user feedback for a particular summary. When prompted (e.g., via dialog box) to provide user feedback, the user may click, for example, the "Ignore" button located at the bottom of the dialog box. Then, the dialog box may disappear. In some embodiments, the user may command a virtual assistant or audio enabled device to ignore the user feedback request.

In some embodiments, the cognitive information summary program 110a, 110b may preclude the user from not providing at least one user feedback for a certain time period or certain number of displayed summaries. In at least one embodiment, the default may be three (3) consecutive displayed summaries. As such, if the user fails to provide user feedback for three consecutive displayed summaries, then the user may not be provided with the "Ignore" button or option when the next summary is displayed. The user may have to provide user feedback for that summary. In another embodiment, such default may be re-configured or changed by an administrator or the user.

In at least one embodiment, the user may provide user feedback at any time. The user may select the "User Feedback" button located at the bottom of the main screen to provide such user feedback. Once the "User Feedback" button is selected, then the user may be prompted (e.g., via dialog box) to provide, in a comment box, the summary or general issues (e.g., improper personal learning style of the user, misleading context included the summaries) that the user feedback is associated with, and click the "Submit" button located at the bottom of the dialog box.

Continuing the previous example, while the summary is playing for RUGBYQA1782, the cognitive information summary program 110a, 110b prompts RUGBYQA1782 by alerting the user with a loud bleeping sound and displaying a dialog box requesting user feedback from RUGBYQA1782. Since RUGBYQA1782 heard the loud bleeping sound, RUGBYQA1782 is aware that user feedback has been requested by the cognitive information summary program 110a, 110b. However, due to limited time, RUGBYQA1782 is unable to provide user feedback at this time. Therefore, RUGBYQA1782 commands the virtual assistant device to ignore the user feedback prompt. The user feedback dialog box then disappears from the screen of the smart phone.

In at least one embodiment, the cognitive information summary program 110a, 110b may utilize an extraction engine to search through the received source(s) of information, and to extract the most used words (e.g., phrases, terms, individual nouns or verbs) by the person or people in the received source(s) of information. The identified most used words by the person or people in the received source(s) of information may be included in the summary presented to user to further explain the pieces of information included in the received source(s) of information to the user. For example, if the instant messaging chats are between three people, the cognitive information summary program 110a, 110b utilizes the extraction engine to identify "disagreed" and "based on the recent team meeting last month" as the most used words by two of three people included in the received instant messaging chats. The cognitive information summary program 110a, 110b will include "disagreed" and "based on the recent team meeting last month" into the summary presented to the user.

In another embodiment, if the user is determined to be a visual learner, then the cognitive information summary program 110a, 110b may generate a series of images conveying the information from the information source. Continuing the previous example, if the user was identified as a visual learner, the cognitive information summary program 110a, 110b will then present a series of flowcharts with images for each of the Brands discussed in the series of emails and a picture of such person, along with their respective title in the company, who stated that the specific brand is the one of the top two brands manufactured by the employer. The flowchart may include any supporting documents next to the specific person that included such supporting documents in the series of emails, as well as an image for each similar competitor brand identified in the email chain. In addition, links with videos or images related to any recent advertisements, social media posts or comments would be included in a separate flowchart and categorized with the brand related to the video or image.

In another embodiment, if the user is determined to be an auditory learner, then the cognitive information summary program 110a, 110b may generate one or more audio files to convey the information from the information source. Continuing the previous example, if the user was identified as an auditory learner, the cognitive information summary program 110a, 110b will then present one audio file in which a summary of the written text in the series of emails is transcribed into an audio recording. The user will then be able to listen to the audio file and any videos related to any recent advertisements, social media posts or comments. In addition, any images, visual representations or documents included in the series of emails or in any recent advertisements, social media posts or comments will be described to the user in the audio file.

Figure 3:
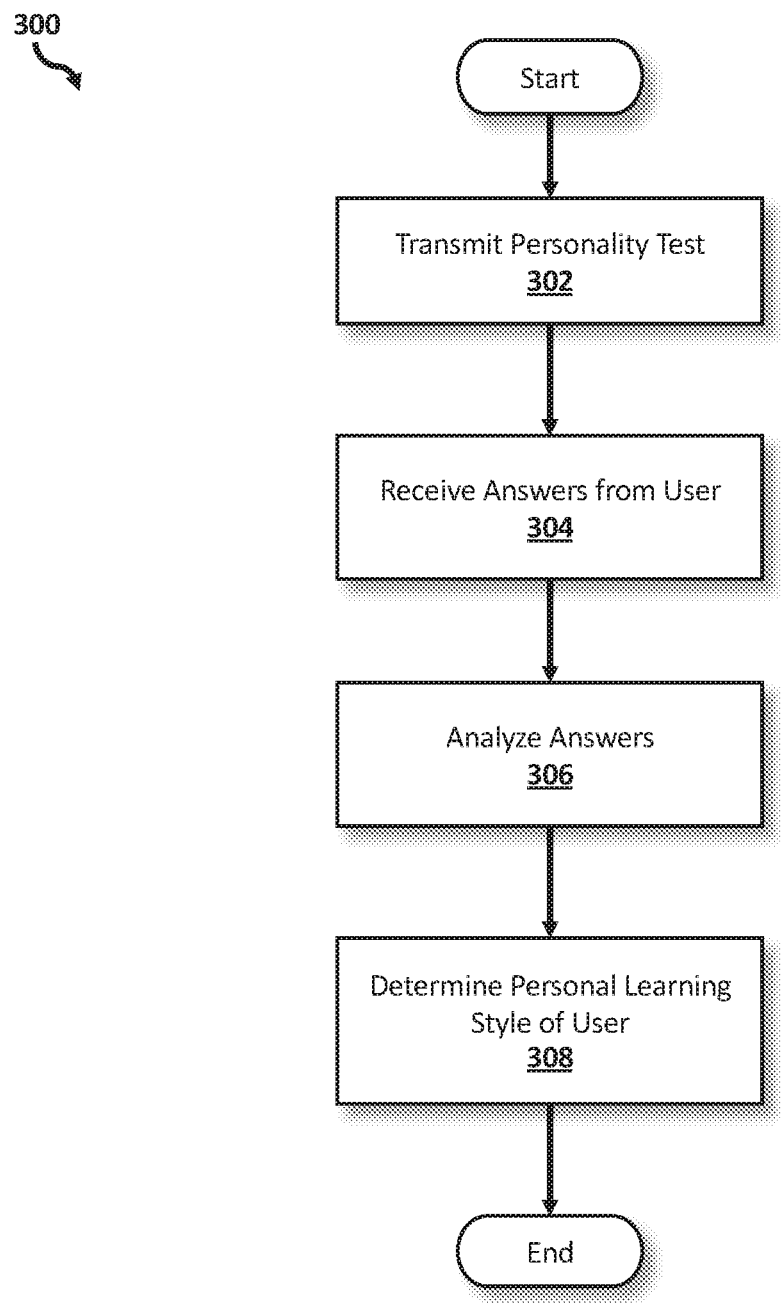
FIG. 3 is an operational flowchart illustrating a process for cognitive personal learning style determination according to at least one embodiment.

Referring now to FIG. 3, an operational flowchart illustrating the exemplary cognitive personal learning style determination process 300 used by the cognitive information summary program 110a, 110b according to at least one embodiment is depicted.

At 302, a personality test is transmitted to the user. Utilizing a software program 108, the personality test may be transmitted, from a test database (e.g., database 114), to the user via communication network 116. The personality test may be based on a standard personality test (e.g., NLP quiz) that determines the personality type of the user based on the beliefs, values, and other factors that affect the user's behavior, social manners and how the user learns information (i.e., personal learning style). The cognitive information summary program 110a, 110b may randomly select the questions included in the personality test from the test database. Alternatively, the cognitive information summary program 110a, 110b may utilize a test engine to select questions based on the data associated with the user profile and the identified user. For example, if the user is a return user and the cognitive information summary program 110a, 110b has difficulty determining whether the personal learning style of the user is kinesthetic or visual, then the test engine may select questions designed to clarify whether the user is kinesthetic or visual.

In some embodiments, the cognitive information summary program 110a, 110b may provide a maximum number of questions that may be included in the personality test in order for the personality test to be brief and quick for the user. In at least one embodiment, the default maximum number of questions may be nine questions for the personality test. In another embodiment, the maximum number of questions may be re-configured or changed by an administrator or the user.

In some embodiments, the cognitive information summary program 110a, 110b may include a minimum number of questions that may be included in the personality test in order for the personality test to be accurate and effective in determining the personal learning style of the user. In at least one embodiment, the default minimum number of questions may be four questions for the personality test. In another embodiment, the minimum number of questions may be re-configured or changed by an administrator or the user.

Additionally, the user may be prompted (e.g., via dialog box) by the cognitive information summary program 110a, 110b, when the personality test is ready for the user to review and provide answers. The dialog box, for example, may include a statement indicating that the user is requested to take a personality test, and further asking the user whether the user is ready to begin with a "Yes" button and "No" button located at the bottom of the dialog box. If the user clicks the "No" button, then a timer, for example, may appear and the user may prompted that the user has a certain amount of time to click the "Yes" button. The user may be precluded from opting out of taking the personality test. As such, the user may not proceed with the cognitive information summary program 110a, 110b until the personality test is taken.

In another embodiment, if the user is return user and has previously taken the personality test, the user may allowed to postpone taking the personality test until the next time that the user starts the cognitive information summary program 110a, 110b. As such, the cognitive information summary program 110a, 110b may proceed with the cognitive information summary process 200 and postpone the cognitive personal learning style determination process 300.

If, however, the user clicks the "Yes" button located at the button of the dialog box, then the dialog box may expand to include the personality test. The user may provide answers to the questions (i.e., user answers) in the personality test within a certain period of time. In some embodiments, the cognitive information summary program 110a, 110b may allot a default amount of 10 minutes to the user to provide answers to the questions in the personality test. In at least one embodiment, the allotted amount of time may be re-configured or changed by an administrator or the user. At the bottom of the expanded dialog box, for example, there may be a "Submit" button. Once the user clicks the "Submit" button, then the expanded dialog box may disappear and the user answers may be transmitted via communication network 116 to the cognitive information summary program 110a, 110b.

In another embodiment, the user may generate a paper copy of the personality test. As such, the user may utilize a writing instrument (e.g., pen, pencil) to answer the questions in the personality test. The user may then manually upload the paper copy of the personality test with the user answers into the cognitive information summary program 110a, 110b.

For example, the user, RUGBYQA1782, noticed that the most recent summaries were interactive games and RUGBYQA1782 experienced difficulty understanding and comprehending the information included in the summaries. As such, RUGBYQA1782 decided to take a new personality test. As such, RUGBYQA1782 clicks the "New Personality Test" button located on the bottom of the main screen, requesting a new personality test. The cognitive information summary program 110a, 110b then randomly selects a new personality test for RUGBYQA1782. The cognitive information summary program 110a, 110b notifies RUGBYQA1782 that the new personality test is ready, and asks RUGBYQA1782 to indicate, by clicking the "Yes" or "No" button located at the bottom of the dialog box, whether RUGBYQA1782 is ready to start. RUGBYQA1782 clicks the "Yes" button and the dialog box immediately expands displaying a new personality test that includes seven questions and a timer showing that RUGBYQA1782 was given 10 minutes to fully respond to the personality test. RUGBYQA1782 completes the new personality test within five minutes and clicks the "Submit" button located at the bottom of the expanded dialog box. The expanded dialog box then disappears.

Next, at 304, answers to the personality test are received from the user. Utilizing a software program 108, the cognitive information summary program 110a, 110b may receive, as input, the answers to the personality test from the user via communication network 116. The cognitive information summary program 110a, 110b may prompt (e.g., via dialog box) the user to confirm that the answers were received.

In another embodiment, if the user manually uploaded user answers via a paper copy into the cognitive information summary program 110a, 110b, then, once the upload has been completed, the cognitive information summary program 110a, 110b may provide a confirmation that the upload process has been completed. For example, the user may be notified (e.g., via dialog box) stating "Upload Completed. Thank you."

Continuing the previous example, shortly after RUGBYQA1782 clicked the "Submit" button at the bottom of the expanded dialog box, RUGBYQA1782 receives a prompt stating "Your answers have been received! Thank you."

Then, at 306, the received user answers are analyzed. Utilizing an analyzer, the cognitive information summary program 110a, 110b may analyze the received user answers. An analysis of the received user answers may be provided to the cognitive information summary program 110a, 110b. Based on the provided analysis, the cognitive information summary program 110a, 110b may determine the personal learning style(s) of the user at 308. The determined personal style(s) of the user, as well as the results of the personality test, may be saved and stored on the user profile in the profile database.

In the present embodiment, the personal learning styles of the user may be based on the Neuro-Linguistic Programming (NLP) personality types (i.e., a psychological approach that involves analyzing strategies used by successful information and applying them to reach a personal goal, and relates to thoughts, language and patterns of behavior learned through experience to specific outcomes). Based on the NLP personality types, the personal learning style(s) of the user may be one of, or a combination of, three main types (e.g., visual, audio or kinesthetic). In another embodiment, one or more other psychological approaches may be utilized to determine the personality type of the user and subsequently the personal learning style of the user.

Continuing the previous example, the analyzer examines the answers provided by RUGBYQA1782 and based on these answers, the cognitive information summary program 110a, 110b determines that RUGBYQA1782 is more of a visual learner than a kinesthetic learner. As such, the cognitive information summary program 110a, 110b saves the results of the personality test and the new determined personal learning style of RUGBYQA1782 to RUGBYQA1782's user profile stored on the profile database.

In at least one embodiment, the profile database, test database and information database may be three separate databases. In another embodiment, the profile database, test database and information database may be a part of one database (e.g., database 114) in which the data associated with each profile database, test database and information database may be indexed separately.

In at least one embodiment, the cognitive personal learning style determination process 300 may commence simultaneously with the cognitive information summary process 200 once the user is identified at 202. The cognitive information summary program 110a, 110b may, however, suspend the cognitive information summary process 200 after the information is analyzed at 206 until the cognitive personal learning style determination process 300 has been completed and the personal learning style of the user is determined at 308. In another embodiment, the cognitive information summary process 200 and cognitive personal learning style determination process 300 may commence consecutively. As such, once the user is identified at 202, then the cognitive information summary process 200 may be suspended, until the cognitive personal learning style determination process 300 has been completed. Then, the cognitive information summary process 200 may continue and receive the information source at 204.

The functionality of a computer may be improved by the cognitive information summary program 110a, 110b because the cognitive information summary program 110a, 110b generates information summaries based on the personal learning style of the user to provide easy handling of the information and improve the user's comprehension and understanding of the information presented and topic discussed in the information source. The cognitive information summary program 110a, 110b further reduces the time of reading and responding to information provided to the user. The inclusion of data associated with the user (e.g., a set of historical data, personality test result(s), personal learning style of the user, a full name of the user, at least one preferred name of the user, at least one email address for the user, at least one most used word utilized by the user, at least one user preference), which may be saved and stored on the profile database, may be utilized to improve the effectiveness of the summary.

It may be appreciated that FIGS. 2 and 3 provide only an illustration of one embodiment and do not imply any limitations with regard to how different embodiments may be implemented. Many modifications to the depicted embodiment(s) may be made based on design and implementation requirements.

Figure 4:
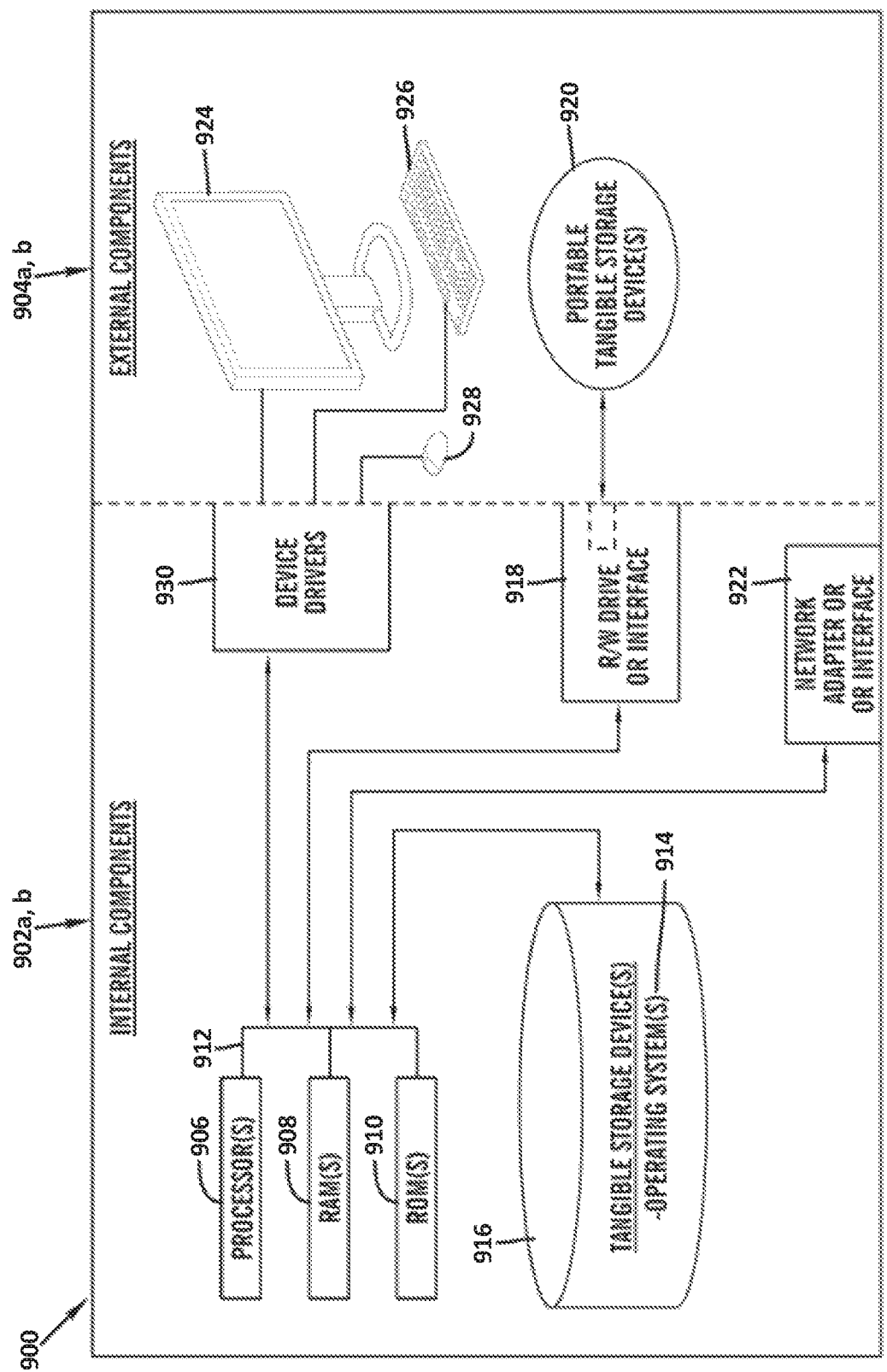
FIG. 4 is a block diagram of internal and external components of computers and servers depicted in FIG. 1 according to at least one embodiment.

FIG. 4 is a block diagram 900 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 4. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the cognitive information summary program 110a in client computer 102, and the cognitive information summary program 110b in network server 112, may be stored on one or more computer-readable tangible storage devices 916 for execution by one or more processors 906 via one or more RAMs 908 (which typically include cache memory). In the embodiment illustrated in FIG. 4, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the cognitive information summary program 110a, 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless wi-fi interface cards, or 3G or 4G wireless interface cards or other wired or wireless communication links. The software program 108 and the cognitive information summary program 110a in client computer 102 and the cognitive information summary program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the cognitive information summary program 110a in client computer 102 and the cognitive information summary program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
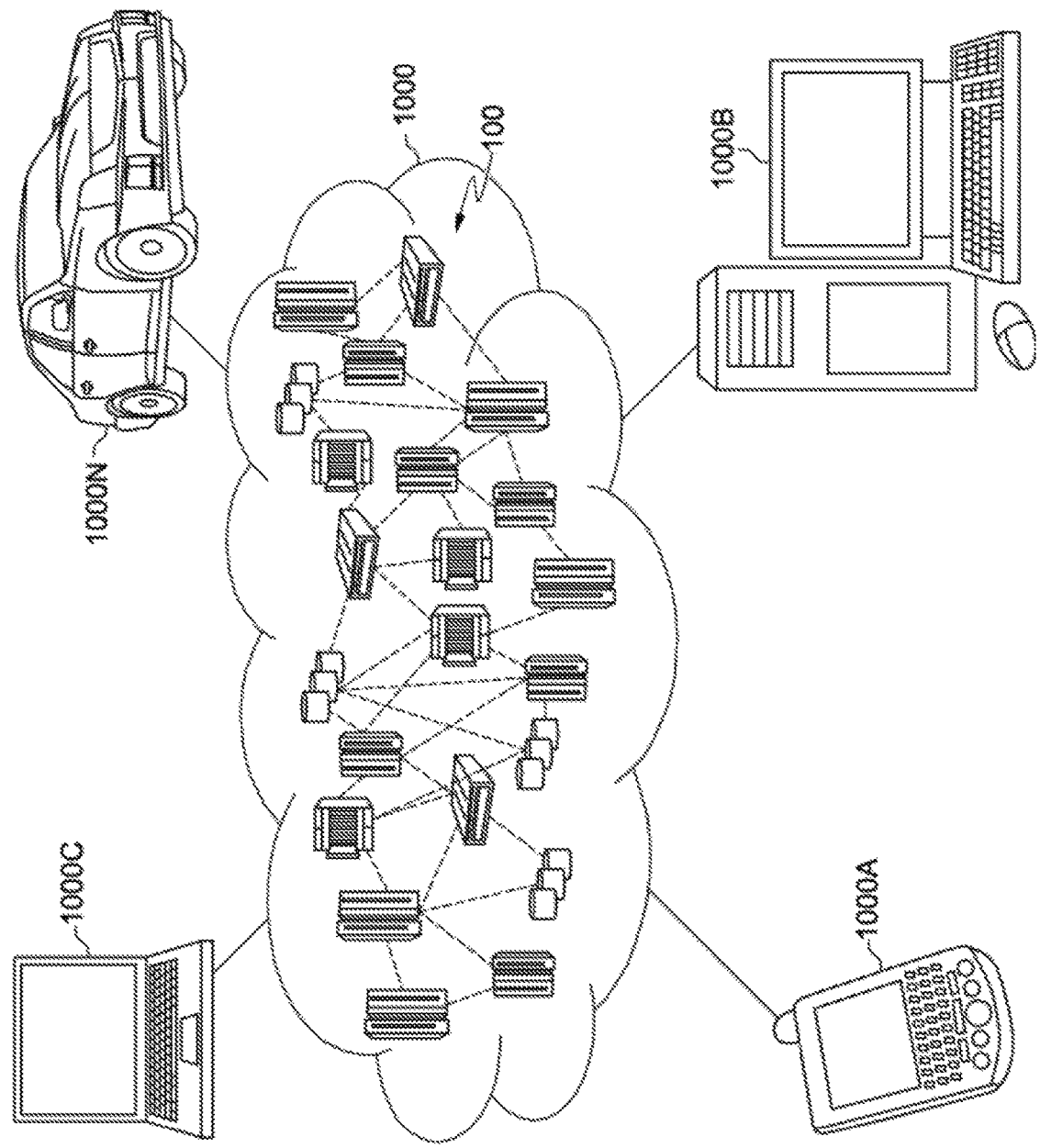
FIG. 5 is a block diagram of an illustrative cloud computing environment including the computer system depicted in FIG. 1, in accordance with an embodiment of the present disclosure.

Referring now to FIG. 5, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 5 are intended to be illustrative only and that computing nodes 100 and cloud computing environment 1000 can communicate with any type of computerized device over any type of network and/or network addressable connection (e.g., using a web browser).

Figure 6:
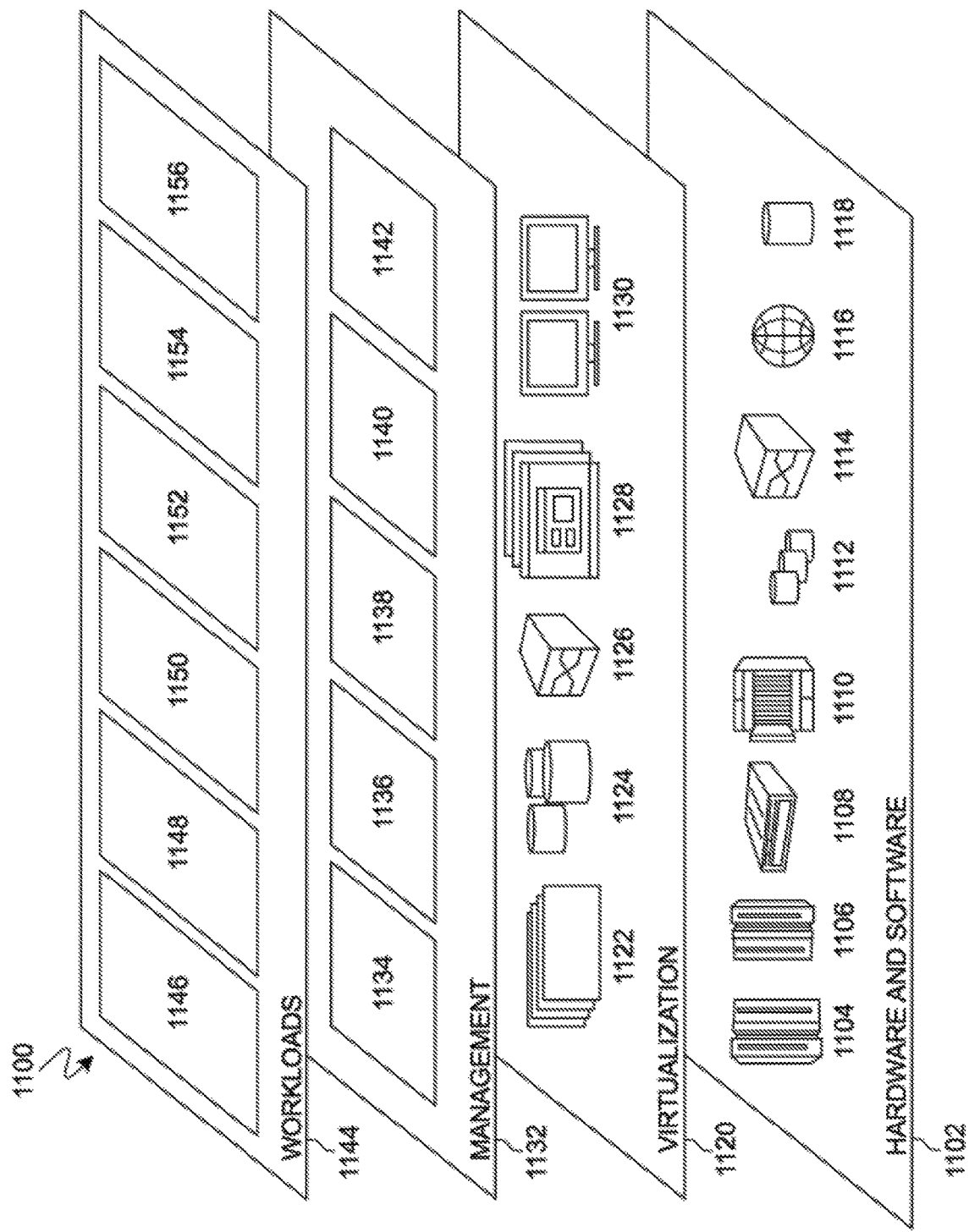
FIG. 6 is a block diagram of functional layers of the illustrative cloud computing environment of FIG. 5, in accordance with an embodiment of the present disclosure.

Referring now to FIG. 6, a set of functional abstraction layers 1100 provided by cloud computing environment 1000 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and cognitive information summary 1156. A cognitive information summary program 110a, 110b provides a way to summarize a piece of information based on the personal learning style of the user.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for summarizing a piece of information based on a personal learning style of a user, the method comprising:
   summarizing the piece of information associated with at least one information source by identifying features of the piece of information comprising at least one repetitive sentence, at least one repetitive term, at least one repetitive phrase, and at least one key word, wherein the identified features are sorted with a corresponding percentage of usage in the at least one information source, wherein an output is generated from the summarized piece of information;
   generating a summary of the piece of information based on the generated output, the personal learning style of the user and a plurality of data associated with the user, wherein the personal learning style of the user is determined by a personality test, wherein the generated summary includes converting the identified features into one or more representations, and wherein the one or more representations are in a form that is consistent with the personal learning style of the user, and wherein the one or more representations are incorporated within the generated summary based on the corresponding percentage of usage of the identified features exceeding a threshold;
   presenting the generated summary to the user; and
   requesting at least one piece of summary feedback from the user in response to presenting the generated summary, wherein requesting the at least one piece of summary feedback from the user further comprises prompting the user to score the summary and provide comments explaining the score via a dialog box.

2. The method of claim 1, wherein presenting the generated summary to the user, further comprises:

providing the user with an option to change the presented summary.

3. The method of claim 1, further comprising:
identifying the user, wherein a user profile is associated with the user;
receiving, from the identified user, the at least one information source; and
analyzing the piece of information included in the at least one information source.

4. The method of claim 3, wherein the plurality of data associated with the user is selected from the group consisting of at least one of the following:
a set of historical data, wherein the set of historical data includes at least one previous personality test result, and the at least one personal learning style of the identified user,
a full name,
at least one preferred name,
at least one email address,
at least one most used word utilized by the identified user, and
at least one user preference.

5. The method of claim 1, wherein generating the summary of the piece of information based on the personal learning style of the user and the plurality of data associated with the user, wherein the personal learning style of the user is determined by the personality test, further comprises:
transmitting, to the user, the personality test, wherein the user responds with answers to the transmitted personality test;
receiving the answers to the transmitted personality test from the user;
analyzing the received answers to the transmitted personality test;
determining the personal learning style of the user based on the analyzed answers to the transmitted personality test; and
storing the analyzed answers to the transmitted personality test and the determined personal learning style of the user on a user profile associated with the user.

6. The method of claim 1, wherein the output is generated from the summarized piece of information, further comprises:
identifying at least one topic discussed in the at least one information source;
extracting a plurality of relevant information from the at least one information source; and
discarding a plurality of irrelevant information from the at least one information source.

7. The method of claim 1, wherein the generated output from the summarized piece of information is selected from the group consisting of at least one of the following:
a list of key words from the at least one information source,
a list of repetitive sentences,
a list of repetitive words,
a list of summary suggestions based on a plurality of user preferences, and
a list of insights associated with at least one topic discussed.

8. The method of claim 1, wherein requesting at least one piece of summary feedback from the user is performed simultaneously with presenting the generated summary to the user.

9. The method of claim 1, wherein requesting at least one piece of summary feedback from the user is performed subsequent to presenting the generated summary to the user.

10. A computer system for summarizing a piece of information based on a personal learning style of a user, comprising:
one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
summarizing the piece of information associated with at least one information source by identifying features of the piece of information comprising at least one repetitive sentence, at least one repetitive term, at least one repetitive phrase, and at least one key word, wherein the identified features are sorted with a corresponding percentage of usage in the at least one information source, wherein an output is generated from the summarized piece of information;
generating a summary of the piece of information based on the generated output, the personal learning style of the user and a plurality of data associated with the user, wherein the personal learning style of the user is determined by a personality test, wherein the generated summary includes converting the identified features into one or more representations, and wherein the one or more representations are in a form that is consistent with the personal learning style of the user, and wherein the one or more representations are incorporated within the generated summary based on the corresponding percentage of usage of the identified features exceeding a threshold;
presenting the generated summary to the user; and
requesting at least one piece of summary feedback from the user in response to presenting the generated summary, wherein requesting the at least one piece of summary feedback from the user further comprises prompting the user to score the summary and provide comments explaining the score via a dialog box.

11. The computer system of claim 10, wherein presenting the generated summary to the user, further comprises:
providing the user with an option to change the presented summary.

12. The computer system of claim 10, further comprising:
identifying the user, wherein a user profile is associated with the user;
receiving, from the identified user, the at least one information source; and
analyzing the piece of information included in the at least one information source.

13. The computer system of claim 12, wherein the plurality of data associated with the user is selected from the group consisting of at least one of the following:
a set of historical data, wherein the set of historical data includes at least one previous personality test result, and the at least one personal learning style of the identified user,
a full name,
at least one preferred name,
at least one email address,
at least one most used word utilized by the identified user, and
at least one user preference.

14. The computer system of claim 10, wherein generating the summary of the piece of information based on the personal learning style of the user and the plurality of data associated with the user, wherein the personal learning style of the user is determined by the personality test, further comprises:
- transmitting, to the user, the personality test, wherein the user responds with answers to the transmitted personality test;
- receiving the answers to the transmitted personality test from the user;
- analyzing the received answers to the transmitted personality test;
- determining the personal learning style of the user based on the analyzed answers to the transmitted personality test; and
- storing the analyzed answers to the transmitted personality test and the determined personal learning style of the user on a user profile associated with the user.

15. The computer system of claim 10, wherein the output is generated from the summarized piece of information, further comprises:
- identifying at least one topic discussed in the at least one information source;
- extracting a plurality of relevant information from the at least one information source; and
- discarding a plurality of irrelevant information from the at least one information source.

16. The computer system of claim 10, wherein the generated output from the summarized piece of information is selected from the group consisting of at least one of the following:
- a list of key words from the at least one information source,
- a list of repetitive sentences,
- a list of repetitive words,
- a list of summary suggestions based on a plurality of user preferences, and
- a list of insights associated with at least one topic discussed.

17. A computer program product for summarizing a piece of information based on a personal learning style of a user, comprising:
- one or more computer-readable storage media and program instructions stored on at least one of the one or more tangible storage media, the program instructions executable by a processor to cause the processor to perform a method comprising:
- summarizing the piece of information associated with at least one information source by identifying features of the piece of information comprising at least one repetitive sentence, at least one repetitive term, at least one repetitive phrase, and at least one key word, wherein the identified features are sorted with a corresponding percentage of usage in the at least one information source, wherein an output is generated from the summarized piece of information;
- generating a summary of the piece of information based on the generated output, the personal learning style of the user and a plurality of data associated with the user, wherein the personal learning style of the user is determined by a personality test, wherein the generated summary includes converting the identified features into one or more representations, and wherein the one or more representations are in a form that is consistent with the personal learning style of the user, and wherein the one or more representations are incorporated within the generated summary based on the corresponding percentage of usage of the identified features exceeding a threshold;
- presenting the generated summary to the user; and
- requesting at least one piece of summary feedback from the user in response to presenting the generated summary, wherein requesting the at least one piece of summary feedback from the user becomes mandatory after a certain time period or certain number of presented summaries.

18. The computer program product of claim 17, wherein presenting the generated summary to the user, further comprises:
- providing the user with an option to change the presented summary.

19. The computer program product of claim 17, further comprising:
- identifying the user, wherein a user profile is associated with the user;
- receiving, from the identified user, the at least one information source; and
- analyzing the piece of information included in the at least one information source.

20. The computer program product of claim 17, wherein generating the summary of the piece of information based on the personal learning style of the user and the plurality of data associated with the user, wherein the personal learning style of the user is determined by the personality test, further comprises:
- transmitting, to the user, the personality test, wherein the user responds with answers to the transmitted personality test;
- receiving the answers to the transmitted personality test from the user;
- analyzing the received answers to the transmitted personality test;
- determining the personal learning style of the user based on the analyzed answers to the transmitted personality test; and
- storing the analyzed answers to the transmitted personality test and the determined personal learning style of the user on a user profile associated with the user.

* * * * *